(12) United States Patent
Feussner et al.

(10) Patent No.: US 7,215,990 B2
(45) Date of Patent: May 8, 2007

(54) DEVICE AND METHOD FOR CARRYING OUT SURGICAL INTERVENTIONS ON A PATIENT

(75) Inventors: Hubertus Feussner, Munich (DE); Rainer Graumann, Höchstadt (DE); Gerd Wessels, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 259 days.

(21) Appl. No.: 10/206,191

(22) Filed: Jul. 29, 2002

(65) Prior Publication Data

US 2003/0040667 A1   Feb. 27, 2003

(30) Foreign Application Priority Data

Jul. 27, 2001   (DE) .............................. 101 36 709

(51) Int. Cl.
*A51B 5/00*   (2006.01)
(52) U.S. Cl. ...................... 600/424; 600/427; 600/429; 606/130

(58) Field of Classification Search ................ 600/407, 600/417, 427, 429, 447, 414; 606/130; 250/203.1; 128/899
See application file for complete search history.

(56) References Cited

U.S. PATENT DOCUMENTS

| | | | | |
|---|---|---|---|---|
| 5,829,444 A | * | 11/1998 | Ferre et al. ................ | 128/897 |
| 5,851,183 A | * | 12/1998 | Bucholz .................... | 600/425 |
| 6,167,296 A | * | 12/2000 | Shahidi .................... | 600/427 |

FOREIGN PATENT DOCUMENTS

| | | |
|---|---|---|
| DE | 197 51 761 A1 | 10/1998 |
| DE | 199 51 502 A1 | 1/2001 |
| WO | 94/23647 | 10/1994 |
| WO | 99/38449 | 8/1999 |

* cited by examiner

*Primary Examiner*—Ruth S. Smith
(74) *Attorney, Agent, or Firm*—Young & Thompson

(57) ABSTRACT

An operating system and method for carrying out surgical interventions on a patient, having a storage device for storing image data of the patient, a surgical instrument, a position sensor fitted on the surgical instrument, and a processing device for calculating, the spatial relationship between the position of the surgical instrument and the organ which is represented by the image data, and for inserting the region of the image data that correspond to the surroundings of the surgical instrument at the correct position into a display device.

11 Claims, 1 Drawing Sheet

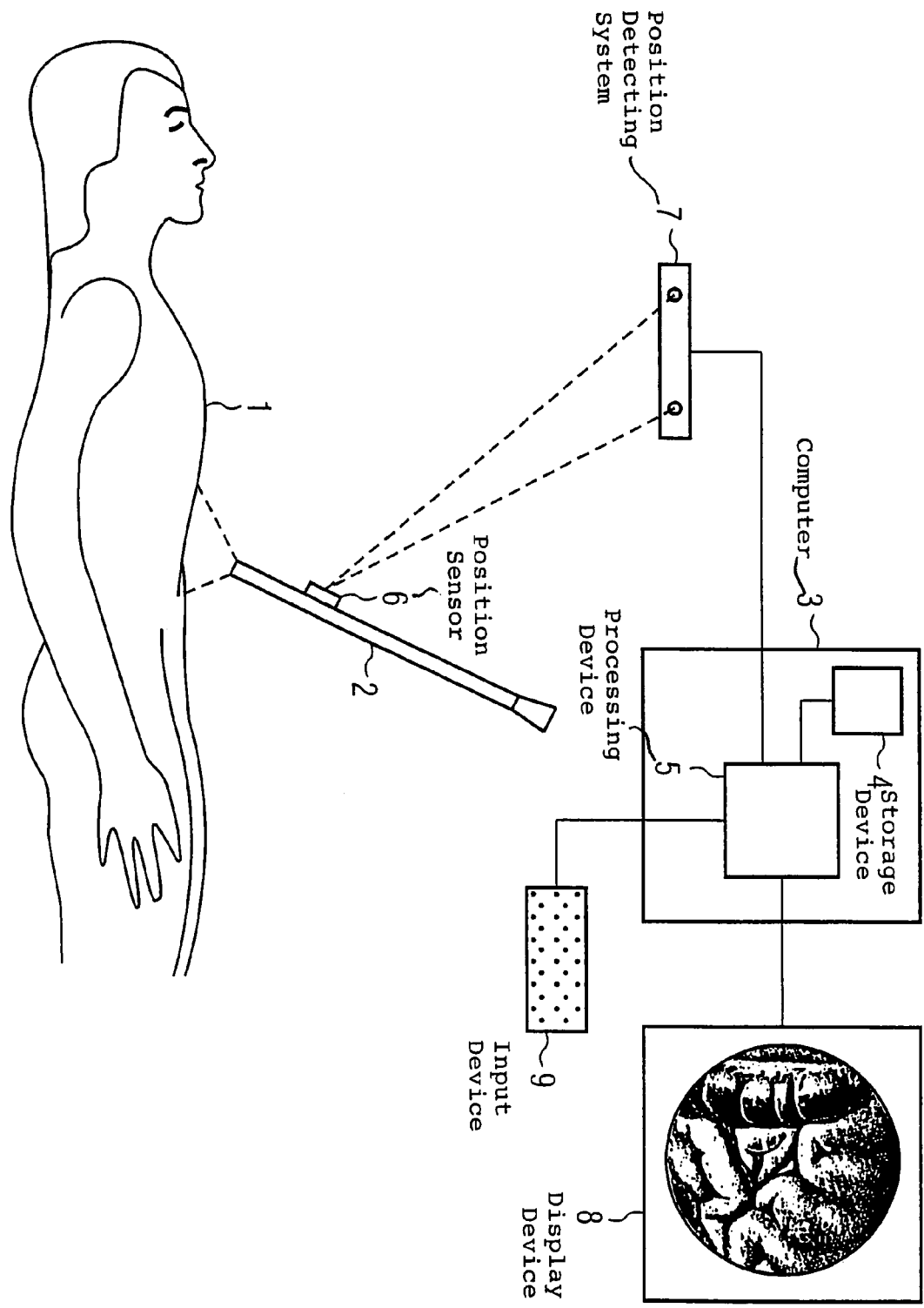

DEVICE AND METHOD FOR CARRYING OUT SURGICAL INTERVENTIONS ON A PATIENT

FIELD OF THE INVENTION

The present invention relates to an operating system for carrying out surgical interventions on a patient, and to a method, applied in this operating system, for displaying image information during a surgical intervention on a patient.

BACKGROUND OF THE INVENTION

In the case of minimally invasive surgical interventions on a patient, the positions for introducing so called trocars, that is to say guide sleeves for surgical instruments such as a laparoscope, for example, into the body of the patient are fixed in the preparatory phase with the aid of an anatomical landmark such as the navel, for example.

Since, however, the position of organs under the skin of the patient is invisible from outside, in many cases the fixed position of the respective trocar is not optimum. This can result in instances of misplacing of the trocars which substantially complicate the subsequent minimally invasive surgical intervention, or even render it impossible in the extreme case.

SUMMARY OF THE INVENTION

It is therefore the object of the present invention to provide an operating system for carrying out surgical interventions on a patient, and a method, applied in this operating system, for displaying image information during the surgical intervention, which render it possible, in a simple way, for a surgical instrument to be introduced into the body of the patient safely and reliably.

This object is achieved by means of an operating system for carrying out surgical interventions on a patient, and a method, applied in this operating system, for displaying image information during the surgical invention.

For this purpose, the operating system according to the invention has a storage device in which image data of the patient or of an organ or region at which the surgical intervention is to be carried out and which are not visible from outside are stored. These data are obtained preoperatively (that is to say before the operation), for example by computer tomography (CT), magnetic resonance (MR) imaging or ultrasonic imaging. These image data can be two- or three-dimensional [lacuna] of the region of the patient (organ).

Furthermore, the operating system according to the invention includes a surgical instrument with the aid of which the intervention is carried out by a surgeon, and a position sensor fitted on this instrument. This position sensor is used to detect the spatial position and situation of the surgical instrument by means of a position-detecting system.

A processing device calculates the spatial relationship between the position of the surgical instrument and the organ which is represented by the image data.

Furthermore, the processing device inserts the image data or at least an image section of the stored image data in a display device, for example display screen, at the correct position with reference to the surgical instrument.

With the aid of the present invention, the surgeon therefore gains an insight covering the organ or the region of the patient under the skin surface or in deeper layers that lies in the "direction of view" or guiding direction of the surgical instrument. The advantage of the present invention consists in that it is possible to determine an optimum position relative to the organ or the lesion, that is to say the region that is to be operated on, for the introduction of the surgical instrument into the body of the patient before the introduction of the instrument.

If a three-dimensional data record is used, the surgeon is also able to obtain depth information of the organ. In this case, he can not only have the organ displayed, as it is represented below the skin surface, but also sectional images of layers of the organ lying therebelow.

Advantageous refinements of the present invention are described in the respective subclaims.

It is advantageous for approximately the middle of the displayed image to correspond to the position of the surgical instrument.

In order to determine the position of the surgical instrument uniquely with reference to the organ, it is possible, in addition, to insert into the displayed image a mark (for example depicted as an arrow or point) that corresponds to the position of the instrument with reference to the organ.

In this case, the surgical instrument can be, for example, a puncture needle, a scalpel, a drill, a cutter, etc.

The present invention is suitable with particular advantage in conjunction with an imaging surgical instrument such as, for example, a laparoscope or an endoscope. In this case, the processing device inserts the organ into the viewing area of the imaging instrument in accordance with the reference to the imaging instrument.

In this way, the surgeon obtains an insight covering the field of view that he would obtain with the laparoscope during the intervention if he introduces the laparoscope by means of a trocar, for example, at a specific point in the body of the patient.

The position of the position sensor, and thus of the surgical instrument can be detected continuously or at regular short time intervals.

BRIEF DESCRIPTION OF THE DRAWING

The present invention is explained in more detail below with the aid of a preferred exemplary embodiment with reference to the attached drawing, in which the attached sole FIG. 1 shows the operating system according to the invention.

DETAILED DESCRIPTION OF THE INVENTION

FIG. 1 shows a patient 1 on whom a surgical intervention is to be undertaken, and a surgical instrument 2 (for example laparoscope) with the aid of which the intervention is undertaken.

The spatial position and situation of the surgical instrument 2 are detected by a position-detecting system that comprises a position sensor 6 fitted on the surgical instrument 2, and a position-detecting device 7.

Furthermore, the operating system according to the invention includes a computer 3 for data processing, having a storage device 4 and a processing device 5.

In accordance with the present invention, image data of a patient that have been obtained preoperatively, for example by means of computer tomography, magnetic resonance imaging or ultrasound, are stored in the storage device 4. These image data in this case include one or more images of internal organs and/or regions of the patient that are to be surgically treated and are invisible from outside. Generated from the images thus obtained is a surface representation that shows the respective organ, for example directly under the abdominal wall or else in deeper layers.

It can be required for the purpose of better representation of the respective organ that the preoperatively obtained data record must be processed, for example by a segmentation or enhancement of the contrast of the organs to be observed.

In accordance with the present invention, the surface images are displayed by the display device 8 during the surgical intervention in a fashion faithful to location and scale. This means that the region of the organ above which the surgical instrument is currently located is displayed at a specific ratio of size. The surgeon therefore has an idea concerning over which point of the organ he is located with the surgical instrument 2, without injuring the patient 1. In the example of FIG. 1, the laparoscope 2 is located over the abdominal wall of the patient 1. In accordance with the present invention, the organs (in the example, the digestive organs) that are located under the abdominal wall are displayed by the display device 8.

In order to implement the present invention, it is necessary to fit a position sensor 6 on the laparoscope 2. Furthermore, it is necessary to use a simple recording procedure to determine the relative spatial relationship between the image data, the surgical instrument 2 and the patient 1. It is thereby possible for the attending physician to guide the laparoscope 2 over the abdominal wall of the patient before setting the trocars, for example, and to obtain a "virtual" impression of the organs lying below the abdominal wall.

It is thereby possible, for example, for trocars or other surgical instruments to be positioned exactly relative to the positions of the internal organs. Since it is possible in the case of the patient 1 for organ displacements to occur between the instant of the operation and the instant of the preceding imaging, an accurate recording is certainly impossible, but also not necessary, since the method presented here is intended only to permit an orientation.

The surgeon is optionally able to examine deeper layers of the organ. A precondition for this is, however, that the stored image data include a three-dimensional image data record. In this case, the surgeon can determine, for example with the aid of the input device 9 (keyboard or mouse), which depth information he requires, that is to say how "far" he would like to look into the patient.

The method presented here can therefore be widened to the use of the laparoscope 2 in the body by virtue of the fact that "virtual" images from the interior of the organs can be superimposed on the laparoscope image.

These "virtual" images can likewise be sectional images from a computer tomograph or magnetic resonance data record with an orientation perpendicular or parallel to the principal axis of the laparoscope (or the surgical instrument), or else surface or volumetric representations. What is important in any case is for the representation to be faithful in terms of location and scale.

The invention claimed is:

1. Operating system for carrying out surgical interventions on a patient, comprising:
   a storage device for storing image data of an organ of a patient that is invisible from outside;
   a surgical instrument for carrying out the surgical intervention;
   a position sensor, fitted on the surgical instrument, for detecting a spatial position of the surgical instrument; and
   a processing device
   i) for calculating a spatial relationship between a position of the surgical instrument located outside the body and the organ, which is represented by the image data, and
   ii) for repeatedly inserting a region of the image data that accurately correspond to the surroundings of the surgical instrument into a display device, the image data being adjustedly inserted to always assure that a center of a displayed image corresponds to an accurate current position of the surgical instrument with reference to the organ of the patient as the surgical instrument is repeatedly repositioned outside the body, so that as the instrument is moved the image data is positioned so that the instrument remains at the center of the display device.

2. The operating system as claimed in claim 1, characterized in that the processing device inserts the position of the surgical instrument in the displayed image at a center of the displayed image, accurately positioned with reference to the organ.

3. The operating system as claimed in claim 1, characterized in that the surgical instrument is an imaging instrument, the processing device inserting the organ into a viewing area of the imaging instrument in accordance with a reference to the imaging instrument.

4. The operating system as claimed in claim 1, characterized in that the position sensor continuously detects the position of the surgical instrument.

5. The operating system as claimed in claim 1, characterized in that the position sensor detects the position of the surgical instrument at intervals.

6. A method for displaying imaging information during a surgical intervention on a patient prior to inserting an instrument into the patient, comprising the steps of:
   storing image data of an organ, of the patient, that is invisible from outside,
   detecting a spatial position of a surgical instrument positioned exterior to the patient and proximate the organ,
   calculating a spatial relationship between the detected spatial position of the surgical instrument and the organ which is represented by the image data, and
   from the calculated spatial relationship and the stored organ image data, repeatedly inserting a region of the organ image data that corresponds to surroundings of the surgical instrument into a display device so as to assure that a center of the displayed region of the patient's organ image continues to accurately correspond to the detected spatial position of the surgical instrument as the surgical instrument is repositioned exterior to the patient, so that as the instrument is moved the organ image is positioned so that the instrument remains at the center of the display device.

7. The method as claimed in claim 6, characterized in that the position of the surgical instrument in the displayed image is inserted at an accurate position with reference to the organ.

8. The method as claimed in claim 6, characterized in that, the surgical instrument used in the detecting step is an imaging instrument, and
   the method further comprises the step of inserting the image data of the organ into a viewing area of the imaging instrument in accordance with a reference to the imaging instrument.

9. The method as claimed in claim 6, characterized in that the position of the surgical instrument is detected continuously.

10. The method as claimed in claim 6, characterized in that the position of the surgical instrument is detected at intervals.

11. An operating system for carrying out surgical interventions on a patient, comprising:
- a storage device for storing image data of an organ, of a patient, that is invisible from outside;
- a surgical instrument;
- a position sensor, fitted on the surgical instrument, for detecting a spatial position of the surgical instrument positioned outside the patient's body and proximate the organ; and
- a processing device for
- i) calculating a present spatial relationship between the spatial position of the surgical instrument outside the body and the organ, and
- ii) for displaying the image data of the patient's organ on a display device as a displayed organ image, with a center of the displayed organ image accurately corresponding to the present position of the surgical instrument outside the body, wherein, the surgical instrument is repositionable into plural positions outside the patient's body and, in each one of the plural positions, the image data is displayed such that the center of the displayed organ image corresponds to the current one of the plural positions, so that as the instrument is moved the organ image is positioned so that the instrument remains at the center of the display device.

* * * * *